United States Patent [19]

Johnson et al.

[11] Patent Number: 4,835,106
[45] Date of Patent: May 30, 1989

[54] ROTOR FOR PROCESSING LIQUIDS USING MOVABLE CAPILLARY TUBES

[75] Inventors: Wayne F. Johnson, Loudon; Carl A. Burtis, Oak Ridge; William A. Walker, Knoxville, all of Tenn.

[73] Assignee: Martin Marietta Energy Systems, Inc., Oak Ridge, Tenn.

[21] Appl. No.: 74,739

[22] Filed: Jul. 17, 1987

[51] Int. Cl.⁴ .......................... G01N 1/10; G01N 21/07
[52] U.S. Cl. ........................................ 436/45; 422/72; 422/101; 436/63; 436/177; 494/16; 494/17
[58] Field of Search .................... 422/72, 101, 102; 436/63, 177, 45; 494/16, 17; 210/512.1, 512.3

[56] References Cited

U.S. PATENT DOCUMENTS

| | | | |
|---|---|---|---|
| 3,901,658 | 8/1975 | Burtis et al. | 422/72 |
| 4,515,889 | 5/1985 | Klose et al. | 435/4 |
| 4,557,660 | 12/1985 | Klose et al. | 356/246 |
| 4,690,899 | 9/1987 | Klose | 422/72 |
| 4,740,472 | 4/1988 | Burtis | 422/72 |
| 4,743,558 | 5/1988 | Guigan | 422/72 |

OTHER PUBLICATIONS

Schultz et al, Clin. Chem., vol. 31, No. 9, 1985.

Primary Examiner—Michael S. Marcus
Attorney, Agent, or Firm—Joseph A. Marasco; Bruce M. Winchell

[57] ABSTRACT

A rotor assembly for processing liquids, especially whole blood samples, is disclosed. The assembly includes apparatus for separating non-liquid components of whole blood samples from liquid components, apparatus for diluting the separated liquid component with a diluent and apparatus for transferring the diluted sample to an external apparatus for analysis. The rotor assembly employs several movable capillary tubes to handle the sample and diluents. A method for using the rotor assembly to process liquids is also described.

15 Claims, 2 Drawing Sheets

ROTOR FOR PROCESSING LIQUIDS USING MOVABLE CAPILLARY TUBES

FIELD OF THE INVENTION

The invention relates to a rotor for processing liquids. More particularly, the invention relates to a rotor for separating a liquid into its solid and liquid components, and diluting a specific aliquot of the liquid component with a diluent.

BACKGROUND OF THE INVENTION

Rotors for processing liquids, along with modifications and improvements, have been previously described in various patents and disclosures. For example, U.S. Pat. No. 3,901,658 issued on Aug. 26, 1975, discloses a rotor assembly for performing photometric analyses using whole blood samples. A gross blood sample is loaded within a centrally located, removable, cell sedimentation bowl and the red blood cells are centrifugally separated from the plasma. The plasma is then displaced from the sedimentation bowl, and measured subvolumes of plasma are distributed to respective sample analysis cuvettes positioned in an annular array about the rotor periphery. Additional means for adding reagents to the respective cuvettes are also disclosed.

Another example of a rotor device useful in processing liquids is described in U.S. patent application Ser. No. 762,368 filed on Aug. 8, 1985, which was publicly disclosed soon thereafter under the Department of Energy licensing program. This application discloses an apparatus for automatic processing and aliquoting of whole blood samples for analysis in a centrifugal fast analyzer. More particularly, this rotor is designed to prepare precise aliquots of serum samples from whole blood and automatically load the serum samples into serum capillaries. This device includes no provision for diluting the serum samples with reagents or other diluents.

U.S. Pat. No. 4,515,889 issued on May 7, 1985, discloses a method for carrying out analytical determinations by mixing and incubating a sample solution with at least one reagent and optically measuring a parameter in the incubated reaction mixture. The mixing, incubating and measuring are carried out during the action of a centrifugal force exerted by rotation of a rotor. This device includes no provision for separating non-liquid components from liquid mixtures.

U.S. Pat. No. 4,557,600 issued on Dec. 10, 1985, discloses a process and device for the centrifugal control and mixing of limited volumes of fluid, especially in the rotor of a centrifugal analyzer. The device includes at least one baffle chamber, in a flow canal for the fluid the volume of which is greater than the volume of fluid. The baffle is shaped such that when the device is rotated at a sufficiently high first speed of rotation, the fluid remains in the chamber. Upon rotation of the rotor at a second lower speed of rotation, the fluid flows out of the baffle chamber as a result of a boundary surface force. Again, this device includes no means for separating non-liquid components of a liquid mixture.

Accordingly, there is a need in the art for a rotor which can provide sample preparation and placement. More particularly, the device must be able to accept a liquid mixture in a capillary tube, spin it down to separate non-liquid components from liquid components, draw a known volume of the liquid component and mix it with a known volume of a diluent, draw a known volume of the diluted liquid component, and place the known volume of diluted liquid component on an analysis test pad.

SUMMARY OF THE INVENTION

The present invention relates to a rotor assembly useful in processing and diluting liquid mixtures for analysis which comprises a rotor body rotatable about an axis of rotation; a separation chamber housed in the rotor body for separating a liquid component from a non-liquid component; a mixing chamber housed in the rotor body for mixing a liquid material with a diluent; a diluent chamber housed in the rotor body for holding a volume of a diluent; a diluent addition port in the rotor body and in fluid connection with the diluent chamber for introduction of a diluent to the diluent chamber; a sample introduction chamber housed in the rotor body and in fluid connection with the separation chamber for introduction of a sample to the separation chamber; a diluted sample retainer associated with the rotor body for retaining a diluted liquid sample; means housed in the rotor body for transferring a predetermined amount of a liquid material from the separation chamber to the mixing chamber; means housed in the rotor body for transferring a predetermined amount of a diluent from the diluent chamber to the mixing chamber; and means housed in the rotor body for transferring a predetermined amount of a liquid material from the mixing chamber to the diluted sample retainer.

The present invention also relates to a method for processing liquids which comprises providing a rotor body rotatable about an axis of rotation having a separation chamber, a mixing chamber, and a diluent chamber; introducing a liquid sample and a liquid diluent to separate locations in the rotor body; rotating the rotor body to transfer the liquid diluent to the diluent chamber, to transfer the liquid sample to the separation chamber and to separate at least one non-liquid component of the liquid sample from at least one liquid component of the liquid sample; stopping the rotation of the rotor body; transferring a predetermined amount of the diluent to the mixing chamber; transferring a predetermined amount of the liquid component of the liquid sample to the mixing chamber; and rotating the rotor body to mix the diluent with the liquid component of the liquid sample.

Accordingly, it is the primary object of the present invention to provide a device that will automatically deliver a specific aliquot of a specifically diluted liquid component of a liquid material to an analysis pad or cuvette.

It is also an object of this invention to provide a blood sample processor that will separate the blood serum from the blood cells, draw a specific aliquot of the blood serum, dilute the aliquot of the blood serum with a specific amount of diluent, draw a specific aliquot of the diluted blood serum, and deliver the aliquot of diluted serum to an analytical test pad or other analysis device.

These and other objects of the present invention will be apparent from the detailed description to follow.

DETAILED DESCRIPTION OF THE PREFERRED EMBODIMENTS

Figure 1:
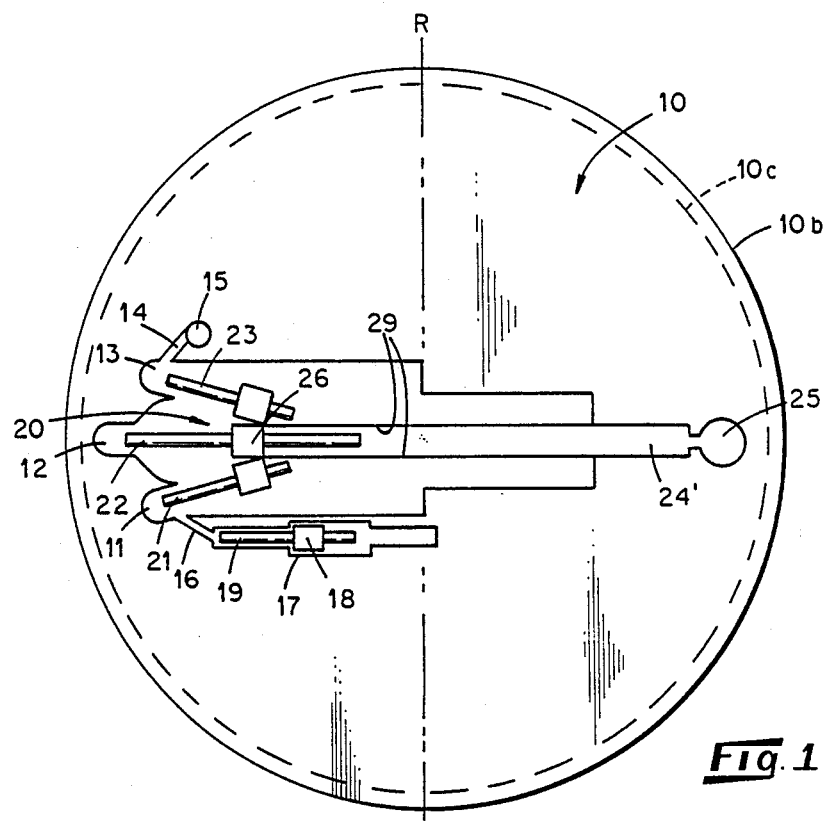
FIG. 1 is a plan view of the rotor of the present invention with the top plate removed and in the sample introduction position.
Figure 2:
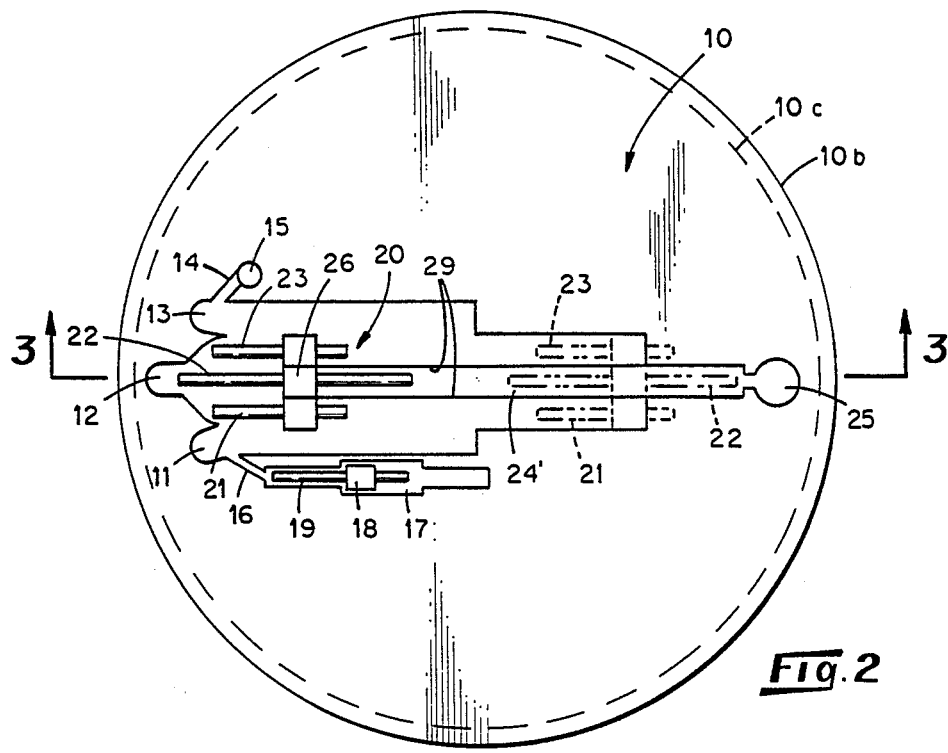
FIG. 2 is a plan view of the rotor of the present invention with the top plate removed and in the liquid mixing position.

In FIG. 1, there is shown a rotor body 10 which can rotate about an axis of rotation R. Rotor body 10 is illustrated in a highly simplified manner and includes a top plate 10a (removed for clarity), a main body 10b, and a bottom plate 10c. The main body 10b includes a separation chamber 11, a mixing chamber 12, and a diluent chamber 13 housed therein. Fluidly connected to the diluent chamber 13 by a diluent channel 14 is a diluent addition port 15. Fluidly connected to the separation chamber 11 by a sample channel 16 is a sample addition port 17. Housed in the sample addition port 17 is a capillary tube holder 18 into which sample tube 19 is inserted by snap-in engagement. Housed in the mixing chamber 12 is a mounting device 20 which is capable of holding three capillary tubes 21, 22 and 23. Capillary tubes 21 and 23 are shown in their sample introduction position. Capillary tubes 21 and 23 are pivotally mounted on mounting device 20 such that they may be rotated into fluid engagement with mixing chamber 12 as shown in FIG. 2. Also depicted in FIG. 1 is groove 24' in which mounting means 20 is slidably located by means of a sliding member 26, and a sample retainer 25.

Referring now to FIG. 2, there is shown rotor body 10 with capillary tubes 21, 22 and 23 in the mixing position. Shown in phantom are capillary tubes 21, 22, and 23 in position to transfer the diluted sample to sample retainer 25.

Figure 3:
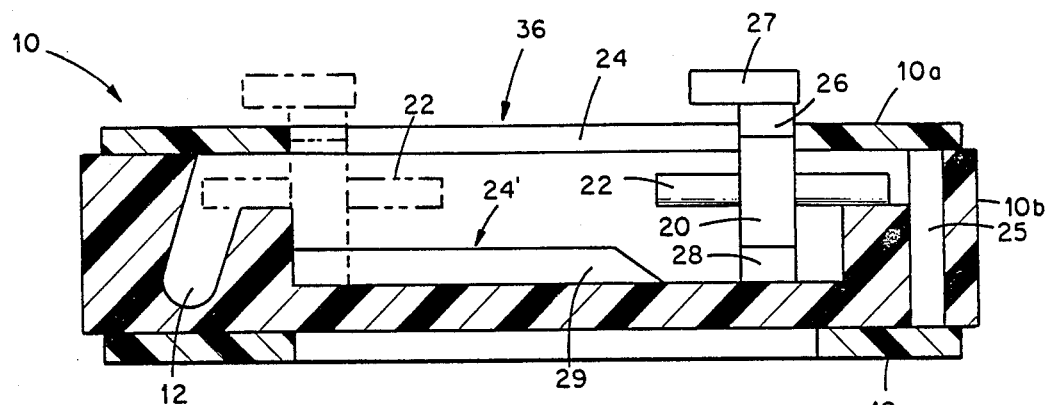
FIG. 3 is a cross-sectional elevation view along line 3—3 of FIG. 2 of one embodiment of the means for transferring the diluted liquid sample from the mixing chamber to a sample retainer.

Referring now to FIG. 3, there is shown a cross-sectional elevation view of the rotor body 10 along line 3—3 of FIG. 2. The capillary tube 22 is shown in position to transfer the sample to sample retainer 25. In phantom is shown capillary tube 22 in the mixing position wherein it is in fluid connection with the mixing chamber 12. Also shown in FIG. 3 is sliding member 26 which slides in a slot 36 defined by guides 24 in top plate 10a. Sliding member 26 is suitably connected to mounting means 20. Attached to sliding member 26 and extending above top plate 10a is a handle 27. The bottom of mounting member 20 is attached to a second sliding member 28 which rides in groove 24' defined by rails 29 in main body 10b.

Figure 4:
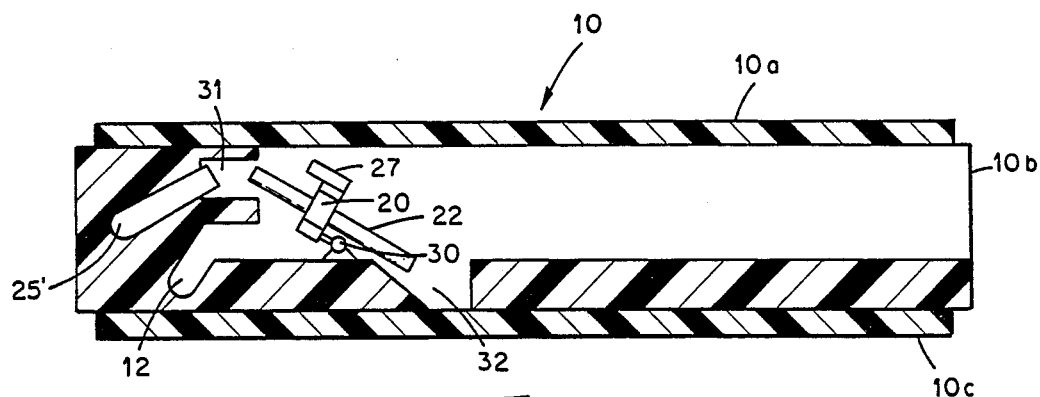
FIG. 4 is a cross-sectional elevation view similar to FIG. 3 showing a second embodiment of the means for transferring the diluted sample from the mixing chamber to a sample retainer.

Referring now to FIG. 4, there is shown an alternate embodiment for the means for transferring a diluted sample from the mixing chamber 12 to sample retainer 25. In this embodiment the mounting member 20 is pivotally mounted on a pivotal mount 30 and the main body 10b includes an additional retainer chamber 31 into which the sample retainer 25 is removably inserted. The capillary tube 22 is pivoted from the mixing chamber 12 to the retainer chamber 31 using the pivotal mount 30. Additionally, there is provided an opening 32 such that the proximal end of the capillary tube 22 clears the main body 10b as the capillary tube 22 is pivoted.

Figure 5:
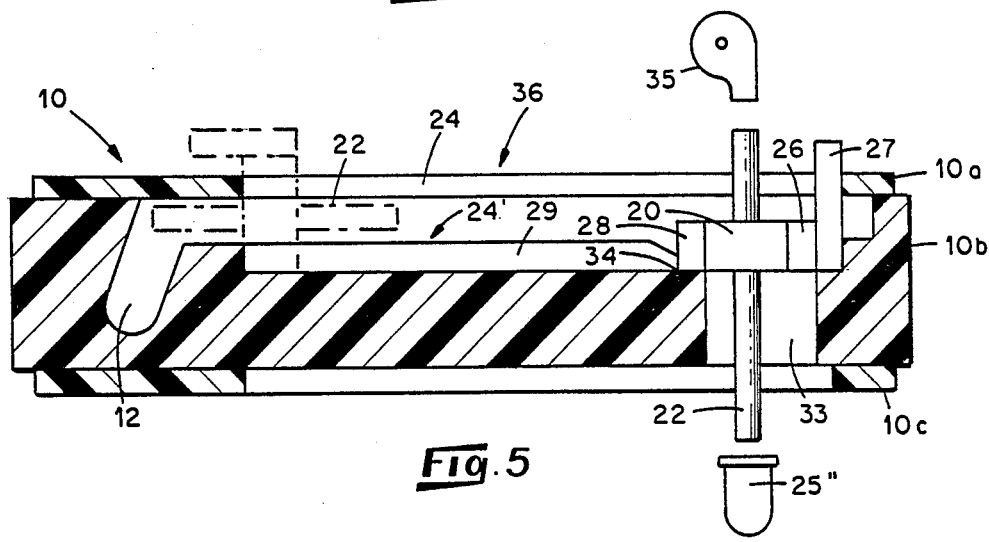
FIG. 5 is a cross-sectional elevation view similar to FIG. 3 showing a third alternative embodiment of the means for transferring the diluted liquid sample from the mixing chamber to a sample retainer.

Referring now to FIG. 5, there is shown a third alternative embodiment of the means for transferring a diluted sample from the mixing chamber 12 to a sample retainer 25''. This embodiment includes an additional opening 33 into which the capillary tube 22 is inserted by a 90 degree rotation of the mounting means 20. The mounting means 20 is caused to rotate 90 degrees by the action of the groove 24' on the sliding member 28. The groove 24' defined by the rail 29 ends at point 34 and does not allow the sliding member 28 to progress any further in that direction. Hence, the mounting member 20 is caused to rotate 90 degrees since the sliding member 26 continues to progress in the slot 36 defined by the guides 24. Also shown is the sample retainer 25 which, in this embodiment, is placed outside the rotor body 10, and a blower 35.

The apparatus as shown in FIG. 1 has the capillary tubes 19, 21, 22 and 23 in the sample introduction position. Capillary tubes 19, 21, 22 and 23 are all removably insertable into the apparatus. Moreover, capillary tubes 21 and 23 are pivotally mounted to mounting means 20 such that they may rotated from a first position wherein they are in fluid connection with the separation chamber 11 and diluent chamber 13 respectively, to a second position wherein they are both fluidly connected to the mixing chamber 12.

Capillary tubes 19, 21, 22 and 23 are all removably mounted in the rotor body 10. Capillary tubes 21, 22 and 23 snap into mounting means 20 by application of a small amount of pressure. Capillary tube 19 also snaps into position in the capillary tube holder 18. All of these capillary tubes are selected to hold a predetermined amount of liquid. This selection allows precise metering of sample, diluent and diluted sample quantities. In addition, the use of capillary tubes provides a simple, automatic method of withdrawing liquids from the diluent, separation and mixing chambers since capillary action will draw liquid into the capillary tubes without the application of additional forces. This makes the device particularly useful in zero gravity conditions where manual liquid handling is extremely difficult. Liquid handling is greatly simplified since precise aliquots of liquid can be withdrawn by merely placing a capillary tube of predetermined size in fluid connection with the liquid. Moreover, this particular method of liquid handling minimizes human involvement and training necessary to prepare liquids for analysis. This, in turn, eliminates many of the difficulties associated with manual sample handling and preparation. For instance, the liquids cannot be spilled and the possibility of contamination is reduced. This automatic method is also faster and more efficient than manual liquid processing.

Presently, the primary use of this device is for processing blood samples into measured, microliter volumes of plasma and diluting these samples for subsequent analysis. In blood sample processing, it is necessary to separate the cells from the serum using a rotor. The present device is also capable of processing blood samples into microliter volumes of plasma and transferring them to a mixing chamber for mixing with a reagent and subsequent analysis. The processing is automatic and does not require human intervention. The device is also useful for automation of a wide variety of analytical methods requiring sample processing, dilution, transfer, mixing and analysis. The device may be widely used in all phases of testing where it is desirable to analyze diluted or undiluted samples in a rotor or some external device.

The device is most useful when it is necessary to separate at least one non-liquid component from at least one liquid component present in the sample. The device is capable of processing most liquids. The diluent may be any of the diluents known to those of ordinary skill in the art. Also, the diluent may be a reagent added to react with the sample in some manner to facilitate analysis.

To use the apparatus, capillary tube 19, containing a liquid material such as blood, is snapped into mounting means 18. Capillary tube 19 is considered the sample tube since its function is to introduce a liquid sample to the apparatus. Then, empty capillary tubes 21, 22 and 23 are attached to mounting means 20 so that capillary tube 21 is positioned in fluid connection with separation chamber 11 and capillary tube 23 is positioned in fluid connection with diluent chamber 13, as shown in FIG. 1. Next, a liquid diluent is introduced to the diluent addition port 15. The rotor body 10 is then rotated about axis R to transfer the sample from the capillary tube 19 through sample channel 16 to separation chamber 11. At the same time, the diluent is transferred from the diluent addition port 15 through the diluent channel 14 to the diluent chamber 13 by the centrifugal force generated by rotation of the rotor body 10.

The rotation of the rotor body 10 continues until the liquid and non-liquid components of the sample are separated from each other in the separation chamber 11. The separation occurs as a result of the centrifugal force generated by rotation of the rotor body 10. At this point, the rotation of the rotor body 10 ceases and the liquid component of the sample in the separation chamber 11 is drawn up by capillary tube 21 which is in fluid connection therewith. At the same time, the liquid diluent in the diluent chamber 13 is drawn up by the capillary tube 23 which is in fluid connection therewith. Each of the capillary tubes 21 and 23 are selected to contain a predetermined volume of liquid. In this manner, the volume of the liquid component of sample, as well as the volume of diluent, is precisely controlled.

The next step in the processing is the pivotal movement of capillary tubes 21 and 23 into the mixing position as shown in FIG. 2. The pivoting of capillary tubes 21 and 23 is accomplished by pivoting the portion of the mounting means 20 to which the capillary tubes 21 and 23 are secured. To facilitate this pivoting, the capillary tubes 21, 22 and 23 are all slidable within the mounting means 20 such that they may be moved radially inwardly or radially outwardly with respect to the mounting means 20. It will normally be necessary to slide capillary tubes 21 and 23 radially inwardly to rotate them from their first position to their second position so that the capillary tubes 21 and 23 will clear the walls between the mixing chamber and the separation and diluent chambers.

In the mixing position, the capillary tubes 21 and 23 are fluidly connected with the mixing chamber 12. The rotor body 10 is then rotated again to thereby discharge the diluent from the diluent capillary tube 23 into the mixing chamber 12, and to discharge the liquid component of the sample from the capillary tube 21 into the mixing chamber 12. Continued rotation of the rotor body 10 results in a thorough mixing of the diluent with the liquid component of the sample in the radially outermost portion of the mixing chamber 12. Once sufficient mixing of the liquid component of the sample with the diluent has occurred, the rotation of the rotor body 10 is stopped. The diluted sample capillary tube 22 which is fluidly connected to the radially outermost portion of the mixing chamber 12 then draws up a predetermined volume of diluted sample from the mixing chamber 12.

Once the diluted sample capillary tube 22 has filled with diluted sample, it is desirable to transfer the diluted sample to some means for retaining the sample so that it can analyzed. One way of transferring the sample to a sample retainer 25 for later analysis, is through the use of the apparatus as shown in FIG. 3. In FIG. 3 diluted sample capillary tube 22 is shown, in phantom, in the mixing position where it is in fluid contact with mixing chamber 12. The diluted sample capillary tube 22 is also shown in a second, sample transfer position wherein it is fluidly connected to the sample retainer 25. The sample retainer 25 may be a cuvette, sample pad or other suitable apparatus.

In this embodiment, the mounting means 20 is slidably mounted in the rotor body 10 by both top sliding member 26 which is slidably engaged in the slot 36 defined by guides 24 in top plate 10a, and lower sliding member 28 which is disposed in the groove 24' defined by rails 29 in main body 10b. Hence, mounting means 20 is capable of sliding from the position shown in phantom in FIG. 3 to the second position shown in solid lines in FIG. 3. Once the diluted sample capillary tube 22 is in the second position, the rotor body 10 is rotated to discharge the diluted sample from the diluted sample capillary tube 22 into the sample retainer 25.

Another means for transferring the diluted sample from the mixing chamber 12 to a removably mounted sample retainer 25 is shown in FIG. 4. In this apparatus, the mounting means 20 is pivotally mounted on the pivotal mount 30 such that the capillary tube 22 can be pivoted from fluid engagement with the mixing chamber 12 to fluid engagement with the retainer chamber 31. Clearance for the capillary tube 22 is provided by opening 32 in the main body 10b. Once the diluted sample capillary tube 22 has drawn up the diluted sample from the mixing chamber 12, the capillary tube 22 is pivoted upward with respect to the main body 10b, into fluid engagement with the retainer chamber 31. Capillary action acts to retain the diluted sample in the diluted sample capillary tube 22 when it is pivoted upward. Once the diluted sample capillary tube 22 is fluidly connected with the retainer chamber 31, the rotor body 10 is rotated to discharge the diluted sample from the diluted sample capillary tube 22 to the sample retainer 25' where the diluted sample is maintained by gravity.

Another alternate embodiment for transferring the diluted sample from the mixing chamber 12 to the sample retainer 25'' is shown in FIG. 5. The mounting means 20 is capable of being pivoted 90 degrees to position the diluted sample capillary tube 22 perpendicular to the plane of the rotor body 10. The pivoting motion is caused by a stopper (not shown) at point 34 in the groove defined by rail 29. This stopper prevents further longitudinal movement of the sliding member 28 and thereby causes a 90 degree rotation of the mounting means 20 since sliding member 26 continues to progress now pivotally into slot 36. Once the capillary tube 22 is perpendicular to the plane of the rotor body 10, a blower 35 is turned on to blow the diluted sample out of the capillary tube 22 into sample retainer 25" located below the rotor body 10. Opening 33 allows enough clearance for the capillary tube 22 to rotate 90 degrees within the rotor body 10.

Another embodiment of the present invention provides for a rotor of the continuous fast analyzing type wherein the mixing chamber 12 also serves as an analysis chamber for analysis of the fluid sample. In this embodiment, the diluted sample capillary tube 22 is omitted from the device and the same procedure is followed until the diluent and sample are mixed in the mixing chamber 12. Once the mixing is complete, analysis is performed in the rotor body 10 through the use of optical analysis means known to those of ordinary skill in the art, without removing the diluted sample from the mixing chamber 12.

It will be appreciated that the instant specification and examples are set forth by way of illustration and not limitation and that various modifications and changes may be made without departing from the spirit and scope of the present invention. Accordingly, the scope of the invention is to be defined by the claims which follow.

What is claimed is:

1. A rotor assembly useful in processing and diluting liquid mixtures for analysis comprising:
    a rotor body rotatable about an axis of rotation;
    a separation chamber housed in said rotor body for separating a liquid component from a non-liquid component;
    a mixing chamber housed in said rotor body for mixing a liquid material with a diluent;
    a diluent chamber housed in said rotor body for holding a volume of a diluent;
    a diluent addition port in said rotor body in fluid connection with said diluent chamber for introduction of a diluent to said diluent chamber;
    a sample introduction chamber housed in said rotor body in fluid connection with said separation chamber for introduction of a sample to said separation chamber;
    a diluted sample retainer associated with said rotor body for retaining a diluted liquid sample;
    movable means housed in said rotor body for transferring a predetermined amount of a liquid material from said separation chamber to said mixing chamber;
    movable means housed in said rotor body for transferring a predetermined amount of a diluent from said diluent chamber to said mixing chamber; and
    movable means housed in said rotor body for transferring a predetermined amount of a liquid material from said mixing chamber to said diluted sample retainer.

2. An apparatus in accordance with claim 1 wherein said diluent addition port and said diluent chamber are oriented such that said diluent is transferred from said diluent addition port to said diluent chamber and wherein said sample introduction chamber and said separation chamber are oriented such that said sample is transferred from said sample introduction chamber to said separation chamber, simultaneously by rotation of said rotor body.

3. An apparatus in accordance with claim 1 wherein said means for transferring a diluent from said diluent chamber to said mixing chamber comprises:
    a pivotally mounted diluent capillary tube having a distal end disposed facing substantially radially outward from the center of said rotor body and a mounting means for mounting said diluent capillary tube for movement from a first position wherein said distal end of said diluent capillary tube is disposed in fluid connection with said diluent chamber to a second position wherein said distal end of said diluent capillary tube is disposed in fluid connection with said mixing chamber.

4. An apparatus in accordance with claim 3 wherein said means for transferring a liquid material from said separation chamber to said mixing chamber comprises:
    a pivotally mounted sample capillary tube having a distal end disposed facing substantially radially outwardly from the center of said rotor body and a second mounting means for mounting said sample capillary tube for movement from a first position wherein said distal end of said sample capillary tube is disposed in fluid connection with said separation chamber to a second position wherein said distal end of said sample capillary tube is disposed in fluid connection with said mixing chamber.

5. An apparatus in accordance with claim 4 wherein said means for transferring a liquid material from said mixing chamber to said diluted sample retainer comprises:
    a capillary tube having first and second ends; and a means for slidably mounting said capillary tube for movement from a first position to a second position such that said first end is disposed substantially radially outwardly from the center of said rotor body and in fluid connection with said mixing chamber when said slidably mounted capillary tube is in said first position, and said second end is disposed substantially radially outwardly from the center of said rotor body and in fluid connection with said diluted sample retainer when said slidably mounted capillary tube is in said second position.

6. An apparatus in accordance with claim 4 wherein said means for transferring a liquid material from said mixing chamber to said diluted sample retainer comprises:
    a pivotally mounted diluted sample capillary tube having a distal end and a third mounting means for mounting said diluted sample capillary tube for movement from a first position wherein said distal end of said diluted sample capillary tube is disposed substantially radially ourwardly from the center of said rotor body and in fluid connection with said mixing chamber to a second position wherein said distal end is disposed substantially radially outwardly from the axis of rotation of said rotor body and in fluid connection with said diluted sample retainer.

7. An apparatus in accordance with claim 4 wherein said means for transferring a liquid material from said mixing chamber to said diluted sample retainer comprises:
    a slidably mounted capillary tube having first and second ends and a third mounting means for mounting said capillary tube for movement from a first position to a second position wherein said first end is disposed substantially radially outwardly from the center of said rotor body and in fluid connection with said mixing chamber when said slidably mounted capillary tube is in said first position;
    a fourth means for pivotally mounting said slidably mounted capillary tube for movement out of the plane of said rotor body when said slidably mounted capillary tube is in said second position; and means for discharging a liquid material from said slidably mounted capillary tube to said diluted sample retainer when said capillary tube is in the second position.

8. An apparatus in accordance with claim 7 wherein said means for discharging comprises:

a means for applying air pressure to one end of said slidably mounted capillary tube.

9. A method of processing liquids comprising:

providing a rotor body rotatable about an axis of rotation, having a separation chamber, a mixing chamber, and a diluent chamber;

introducing a liquid sample and a liquid diluent to separate locations in said rotor body;

rotating said rotor body to transfer said liquid diluent to said diluent chamber, to transfer said liquid sample to said separation chamber and to separate at least one non-liquid component of said liquid sample from at least one liquid component of said liquid sample;

stopping the rotation of said rotor body;

transferring via movable means housed in said rotor a predetermined amount of said diluent to said mixing chamber;

transferring via movable means housed in said rotor a predetermined amount of said liquid component of said liquid sample to said mixing chamber; and rotating said rotor body to mix said diluent with said liquid component of said liquid sample.

10. A method in accordance with claim 9 wherein said step of transferring a predetermined amount of said diluent to said mixing chamber comprises:

providing a pivotally mounted capillary tube of predetermined size in fluid connection with said mixing chamber such that upon stopping said rotor said diluted sample fills said capillary tube;

pivoting said capillary tube into fluid connection with said mixing chamber; and subsequently rotating said rotor such that the contents of said capillary tube is discharged into said mixing chamber.

11. A method in accordance with claim 9 wherein said step of transferring a predetermined amount of said liquid component of said liquid sample to said mixing chamber comprises:

providing a pivotally mounted capillary tube of predetermined size in fluid connection with said separation chamber such that upon stopping said rotor said diluted sample fills said capillary tube;

pivoting said capillary tube into fluid connection with said mixing chamber; and subsequently rotating said rotor such that the contents of said capillary tube is discharged into said mixing chamber.

12. A method in accordance with claim 9 further comprising the steps of:

providing a sample retaining means;

stopping the rotation of said rotor body after said mixing step; and moving via movable means housed in said rotor said diluted sample from said mixing chamber to said sample retaining means.

13. A method in accordance with claim 12 wherein said step of moving said diluted sample to a sample retaining means comprises:

providing a capillary tube in fluid connection with said mixing chamber such that upon stopping said rotor said diluted sample flows into said capillary tube;

moving said capillary tube into fluid connection with said sample retaining means; and discharging the contents of said capillary tube into said retaining means.

14. A method in accordance with claim 9 further comprising the steps of:

providing a means for analyzing; and analyzing said diluted sample using said means for analyzing.

15. A method in accordance with claim 14 further comprising the steps of:

stopping the rotation of said rotor body after said mixing step; and automatically transferring said diluted sample to a means for analyzing said diluted sample.

* * * * *